US00PP13923P29

(12) United States Plant Patent
Turner

(10) Patent No.: US PP13,923 P2
(45) Date of Patent: Jul. 1, 2003

(54) BRACTEANTHA PLANT NAMED 'ROSE PINK'

(75) Inventor: Matthew Turner, Penrith South (AU)

(73) Assignee: Oasis Horticulture Pty. Ltd. (AU)

( * ) Notice: Subject to any disclaimer, the term of this patent is extended or adjusted under 35 U.S.C. 154(b) by 0 days.

(21) Appl. No.: 10/109,494

(22) Filed: Mar. 27, 2002

(51) Int. Cl.[7] ..... A01H 5/00
(52) U.S. Cl. ..... Plt./359
(58) Field of Search ..... Plt./359

(56) References Cited

U.S. PATENT DOCUMENTS

PP10,742 P * 12/1998 Bautista ..... Plt./359

* cited by examiner

*Primary Examiner*—Bruce R. Campell
*Assistant Examiner*—Susan B. McCormick
(74) *Attorney, Agent, or Firm*—Wood, Phillips, Katz, Clark & Mortimer

(57) ABSTRACT

A new and distinct Bracteantha plant named 'Rose Pink', characterized by its upright mounded growth habit, dark pink involucral bracts and yellow disc florets and dark green leaves.

1 Drawing Sheet

LATIN NAME OF THE GENUS AND SPECIES OF PLANT CLAIMED

*Bracteantha bracteata.*

VARIETY DENOMINATION

'Rose Pink'.

BACKGROUND OF THE INVENTION

The present invention comprises a new and distinct Bracteantha plant, botanically known as *Bracteantha bracteata* and hereinafter referred to by the cultivar name 'Rose Pink'.

The new cultivar was developed by the inventor through a controlled breeding program at New South Wales, Australia in March, 1998.

The female (seed) parent of 'Rose Pink' was the proprietary Bracteantha selection designated B98-12A5 (not patented in the United States), which exhibits yellow involucral bract color. The male (pollen) parent of 'Rose Pink' was the proprietary Bracteantha selection designated 26A (not patented in the United States) which exhibits yellow involucral bract color. 'Rose Pink' was selected as one of the flowering progeny of the above stated cross on Aug. 1, 1998.

Asexual reproduction of the new cultivar by terminal cuttings, at West Chicago, Ill., has demonstrated that the characteristics of the new cultivar as herein described are firmly fixed and retained through successive generations of such asexual propagation.

SUMMARY OF THE INVENTION

It was found that the cultivar of the present invention:

(a) exhibits dark pink involucral bracts and yellow disc florets;

(b) forms dark green foliage;

(c) exhibits a good basal branching character; and (d) exhibits an upright mounded growth habit.

When the new cultivar of the present invention is compared to 'Antique Shades' (disclosed in U.S. Plant patent application Ser. No. 09/819,272) it is found that the new cultivar has smaller leaves and has flowers of darker pink.

BRIEF DESCRIPTION OF PHOTOGRAPH

The accompanying photograph show as nearly true as it is reasonably possible to make the same in color illustrations of this type, typical flower and foliage characteristics of the new cultivar. The photograph illustrates two plants in one pot, grown for 10 weeks in a greenhouse at West Chicago, Ill.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length.

The chart used in the identification of colors described herein is The R.H.S. Colour Chart of The Royal Horticultural Society, London, England. The color values were determined on Feb. 6, 2002. The readings were taken between 10:00 and 11:00 a.m. under natural daylight conditions. The plants were produced from cuttings taken from stock plants and grown for 12 weeks in a double polycarbonate covered greenhouse under conditions comparable to those used in commercial practice while utilizing a soilless growth medium. Temperatures of approximately 65° to 75° (18° to 24° C.) during the day and approximately 55° to 60° F. (13° to 16° C.) during the night and light levels of between 5,000 and 8,000 footcandles were maintained.

Classification:

*Botanical.*—*Bracteantha bracteata* cultivar 'Rose Pink'.

*Commercial.*—Helichrysum.

Parentage:

*Female parent.*—Proprietary Bracteantha selection designated B98-12A5.

*Male parent.*—Proprietary Bracteantha selection designated 26A.

Propagation:

*Type cutting.*—*Terminal tip.*

*Time to initiate roots.*—Approximately 21 to 30 days with the shorter times generally being experienced in the summer and the longer times in the winter.

Plant description:

*Form.*—Upright, mounded.

*Habit of growth.*—Moderate. A mature plant, 12 weeks after the planting of a rooted cutting, measures approximately 19.8 cm in height and approximately 38.8 cm in diameter.

*Branching habit.*—Freely basal branching although pinching improves basal branching. Develops approximately 5 lateral branches.

*Lateral branch.*—Length: Approximately 24 cm. Diameter: Approximately 5 mm. Surface texture: Hirsute. Color: 144B. Internode length: Approximately 5 mm.

*Foliage.*—Arrangement: Alternate. Shape: Linear with entire margin, acute apex and clasping base. Size: Approximately 4.5 cm in length and approximately 6 mm at widest point. Upper surface texture is rough and color is darker than 147A. Lower surface texture is smooth and color is 147B. Midvein on lower surface is moderately pubescent. Venation of both surfaces: Closest to 145B.

Flowering description:

*Flowering habit.*—Freely flowering.

*Natural flowering season.*—Spring through fall.

Flower description:

*Inflorescence type.*—Single, composite.

*Fragrance.*—None.

*Bud.*—Size: 1.9 cm in length, and 2 cm in diameter. Color: Lighter than 145D at base and 71A at tip.

*Inflorescence*—Diameter: Approximately 3.3 cm. Depth: Approximately 1.8 cm.

*Involucral bracts.*—Quantity: Approximately 60 arranged in 6 whorls. Aspect: Appear flat at maturity then become downwardly pointing with age. Texture: Smooth, papery. Shape: Linear. Size: Length is approximately 9 mm, width varies from 1 mm (inner whorl) to 4 mm (outer whorl). Color — Upper and lower surfaces, fully opened: 71B with tip of 71A and base of 155D.

*Disc diameter.*—1.7 cm.

*Disc florets.*—Shape: Tubular. Length: Approximately 6 mm. Color: 23A.

*Peduncle.*—Length: Approximately 6 cm. Strength: Good. Aspect: Erect. Color: 146C. Texture: Puberulent.

*Reproductive organs.*—Androecium — Stamen number: 1. Anther color: 23B. Pollen color: 25A. Gynoecium — Pistil number:1. Pistil length: 1 cm. Stigma shape: Bilobate. Stigma color: 21B. Style length: 5 mm. Style color: 1B.

Disease resistance: Resistance to diseases common to Helichrysum has not been observed.

Seed development: Seed development has not been observed.

I claim:

1. A new and distinct Bractheantha plant named 'Rose Pink' substantially as herein shown and described, which:

(a) exhibits dark pink involucral bracts with yellow disc florets;

(b) forms dark green foliage;

(c) exhibits a good basal branching character; and (d) exhibits an upright mounded growth habit.

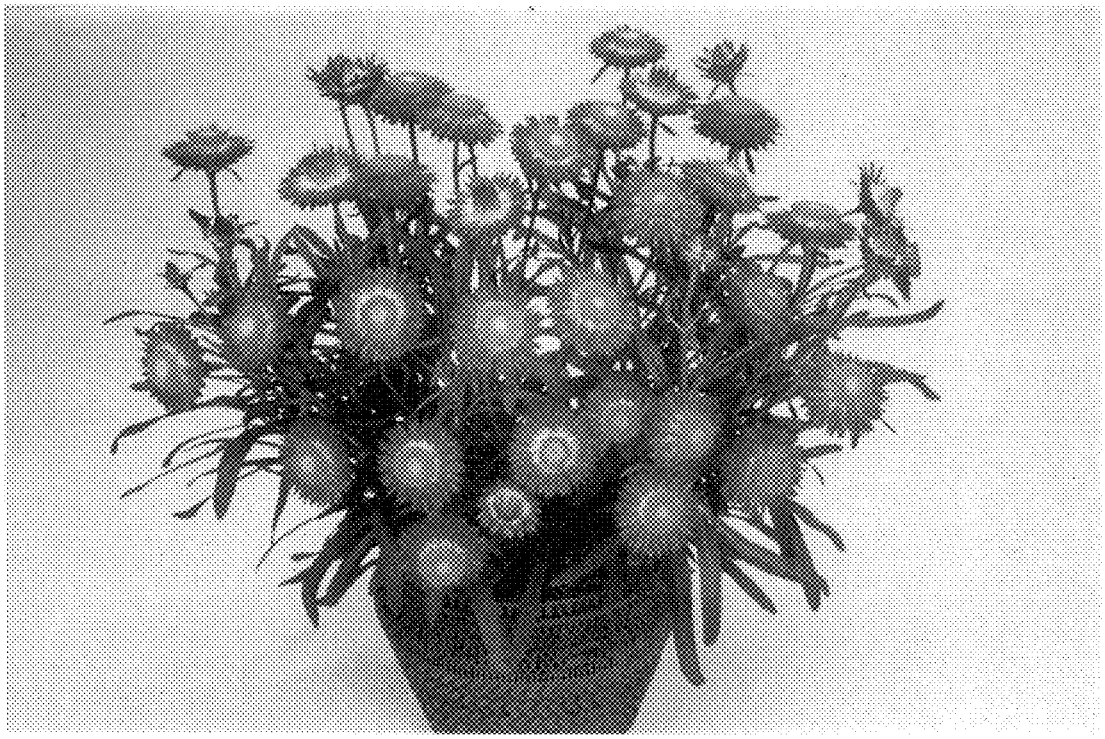

* * * * *